US012805909B2

(12) United States Patent
Holderness

(10) Patent No.: US 12,805,909 B2
(45) Date of Patent: Nov. 24, 2026

(54) PEDICLE SCREW REMOVAL SYSTEM AND METHOD

(71) Applicant: Chandler Holderness, Franktown, CO (US)

(72) Inventor: Chandler Holderness, Franktown, CO (US)

( * ) Notice: Subject to any disclaimer, the term of this patent is extended or adjusted under 35 U.S.C. 154(b) by 0 days.

(21) Appl. No.: 19/352,581

(22) Filed: Oct. 8, 2025

(65) Prior Publication Data

US 2026/0315113 A1 Oct. 15, 2026

Related U.S. Application Data

(60) Provisional application No. 63/788,998, filed on Apr. 15, 2025.

(51) Int. Cl.
*A61B 17/70* (2006.01)

(52) U.S. Cl.
CPC ...... *A61B 17/7002* (2013.01); *A61B 17/7007* (2013.01); *A61B 17/7037* (2013.01)

(58) Field of Classification Search
CPC ............ A61B 17/8875; A61B 17/7091; A61B 17/7076; A61B 17/7082
See application file for complete search history.

(56) References Cited

U.S. PATENT DOCUMENTS 4,078,458 A 3/1978 Berendzen
5,207,131 A 5/1993 Pool et al.
8,920,422 B2 12/2014 Homeier et al.
9,517,065 B2 12/2016 Simms et al.
10,792,079 B1 * 10/2020 Hamade ............. A61B 17/7082
10,820,936 B2 * 11/2020 Ortiz .................. A61B 17/7082
12,369,956 B2 * 7/2025 Jenkins .............. A61B 17/7091
2004/0097947 A1 * 5/2004 Wolford ............ A61B 17/1617 606/80
2005/0228400 A1 10/2005 Chao et al.
(Continued)

FOREIGN PATENT DOCUMENTS

CN 110840546 A 2/2020
WO 99/56662 A2 11/1999

OTHER PUBLICATIONS

Rahimizadeh, et al., "Retrieving Polyaxial Tulip-head Pedicle Screws in Revision Spine Surgery: a Technical Note", Iranian Jornal of Neurosurgery, 2024, vol. 10, E8, 3 pages.
(Continued)

*Primary Examiner* — Andrew Yang
(74) *Attorney, Agent, or Firm* — Whiteford, Taylor & Preston, LLP; Jeffrey Schell

(57) ABSTRACT

A universal pedicle screw removal system featuring a straight cylindrical cross rod integrated with a hollow tubular main shaft for comprehensive set screw manipulation. The system achieves 98% compatibility with existing pedicle screw configurations by utilizing standardized rod dimensions of 5.5-6.0 millimeters and enabling reuse of original set screws. A mechanically interlocked geometric interface at the superior end provides secure handle attachment for controlled torque application. This pre-fabricated, single-piece design eliminates intraoperative assembly requirements while providing a cost-effective alternative to expensive universal removal sets, reducing risks associated with forceful extraction techniques.

19 Claims, 10 Drawing Sheets

(56) References Cited

U.S. PATENT DOCUMENTS

| | | | |
|---|---|---|---|
| 2010/0121385 | A1 | 5/2010 | Blain et al. |
| 2011/0282361 | A1 | 11/2011 | Miller et al. |
| 2012/0203288 | A1 | 8/2012 | Lange et al. |

OTHER PUBLICATIONS

Gupta R, et al., “Hollow mill for extraction of stripped titanium screws: an easy, quick, and safe technique”, J Surg Tech Case Rep. Jan. 2014;6(1):9-11. doi: 10.4103/2006-8808.135135. PMID: 25013544; PMCID: PMC4090986.

Innovating Celebrating Collaborating, Innomed Revision instruments—screw removal, https://www.innomed.net/revision_screwremoval.htm, retrieved Jun. 22, 2026, 12 pages.

Johnson&Johnson MedTech, Intended for healthcare professionals, The next era of medtech is here, 9 pages, https://www.jnjmedtech.com, retrieved Jun. 22, 2026, 9 pages.

Kose KC, et al., “Easy retrieval of polyaxial tulip-head pedicle screws by “U” rod technique”, Eur Spine J. Jan. 2010; 19 (1):144-6. doi: 10.1007/s00586-009-1096-4. Epub Jul. 18, 2009. PMID: 19618219; PMCID: PMC2899743.(Abstract).

Medfix Lumbar Screw Removal Set, https://medfix.com, retrieved Jun. 22, 2026, 4 pages.

Shukla Medical Copter, universal Pedicle Screw Construct Removal Solution, https://www.shuklamedical.com/products/copter, retrieved Jun. 22, 2026, 2 pages.

Elmadağ M, Güzel Y, Uzer G, Acar MA. An innovative universal screw removal instrument. Korean J Spine. Mar. 2015;12(1):1-4. doi: 10.14245/kjs.2015.12.1.1. Epub Mar. 31, 2015. PMID: 25883660; PMCID: PMC4398821.

Provisional Patent Application: “Pedicle Screw Removal System and Method.” and accompanying figures. Provided by client, 2025, 17 pages.

* cited by examiner

PEDICLE SCREW REMOVAL SYSTEM AND METHOD

CROSS REFERENCE TO RELATED APPLICATIONS

This application claims the benefit of and priority to U.S. Provisional Patent Application No. 63/788,998, filed Apr. 15, 2025, entitled "PEDICLE SCREW REMOVAL SYSTEM AND METHOD," naming Chandler Holderness as inventor, under 35 U.S.C. § 119 (e). The disclosure of the above-referenced provisional application is hereby incorporated by reference in its entirety.

BACKGROUND OF THE INVENTION

In spinal surgery, the removal of pedicle screws is often necessary due to various medical conditions and complications. These situations include adjacent level disease requiring additional levels of fusion, nonunion, hardware problems, or any issues with a previously performed spinal fusion that necessitate pedicle screw removal.

Currently, several challenges exist with pedicle screw removal procedures. One significant problem is identifying and obtaining the correct drivers for specific pedicle screws. From X-rays, it can be impossible to determine the manufacturer of the pedicle screw which often determines appropriate fit for the removal mechanism, making it difficult to identify the correct interface. Additionally, the internal mechanism of these screws can become degraded over time complicating the removal process.

While universal pedicle screw removal sets exist as a solution, they present their own set of challenges. Firstly, these sets are extremely expensive, often costing tens of thousands of dollars. In many cases this relates to the large number of bits required to include within each universal pedicle screw removal set to maximize the applicability to the widest variety of pedicle screw configurations. Furthermore, the bits in these sets can go missing or become worn out over time. In some cases, even when surgeons successfully remove the pedicle set screw, they may still be unable to extract the pedicle screw from the bone.

Most hospitals maintain universal pedicle screw removal sets, and while many set screws can be removed using a standardized T25 driver, there are instances where no bit fits with the bone screw's proprietary engagement point. When conventional removal methods fail, surgeons must resort to more aggressive techniques, often involving the application of raw force. This approach carries significant risks, including potentially pedicle fracture, excessive trauma to surrounding tissue, screw fracture during removal, and challenges associated with the polyaxial aspects of a pedicle screw, which facilitate the appropriate placement of rods but complicate the removal by creating difficulty in accordance with the application of torque during removal processes.

A need therefore remains for a universal pedicle screw removal tool that is compatible with the vast majority of existing pedicle screws, eliminating the need to identify specific manufacturers or maintain extensive sets of specialized removal bits. Such a solution should be able to effectively interface with standard pedicle screw configurations, particularly in cases where conventional universal removal sets lack the appropriate bit for the bone screw's proprietary engagement point. Furthermore, there is a need for a solution that reduces the risks associated with forceful removal techniques while providing a reliable method for extracting pedicle screws, even in cases where the internal mechanisms have degraded or when the set screw has been successfully removed but the pedicle screw remains fixed in the bone.

SUMMARY OF THE INVENTION

The present invention in a preferred embodiment provides a universal pedicle screw removal system designed to address the challenges associated with extracting previously implanted pedicle screws during spinal surgery procedures. The system comprises several key components that work in concert to provide a universal solution compatible with approximately 98% of existing pedicle screw configurations.

The system includes a tubular main shaft with a hollow channel that accommodates set screw manipulation, a cross rod for secure engagement with the pedicle screw tulip, and a superior interface that accepts various handle configurations for torque application. The hollow tubular main shaft, approximately 1-2 centimeters in diameter, enables placement and manipulation of set screws through its central channel during the removal procedure.

The cross rod is specifically designed to interface with standard pedicle screw tulips and is compatible with common rod sizes of 5.5 and 6.0 millimeters. This standardized sizing ensures broad compatibility since rod sizes are relatively standard across different pedicle screw manufacturers. The system uniquely enables the reuse of the original set screw removed from the patient's pedicle screw, eliminating the need to identify specific manufacturers or maintain extensive sets of specialized removal bits.

The superior aspect of the device features a geometric configuration that creates a mechanically interlocked interface through a tube cap, ensuring efficient transfer of applied torque from the handle through the assembly to the secured pedicle screw. This integrated design eliminates the need for extensive universal removal sets while providing a reliable method for extracting pedicle screws, even in cases where conventional removal methods may fail.

DETAILED DESCRIPTION

The preferred embodiment of the present invention provides a universal pedicle screw removal system that addresses the challenges associated with extracting previously implanted pedicle screws during spinal surgery procedures. The system comprises several key components that work in concert to provide a universal solution compatible with approximately 98% of existing pedicle screw configurations.

Figure 1:
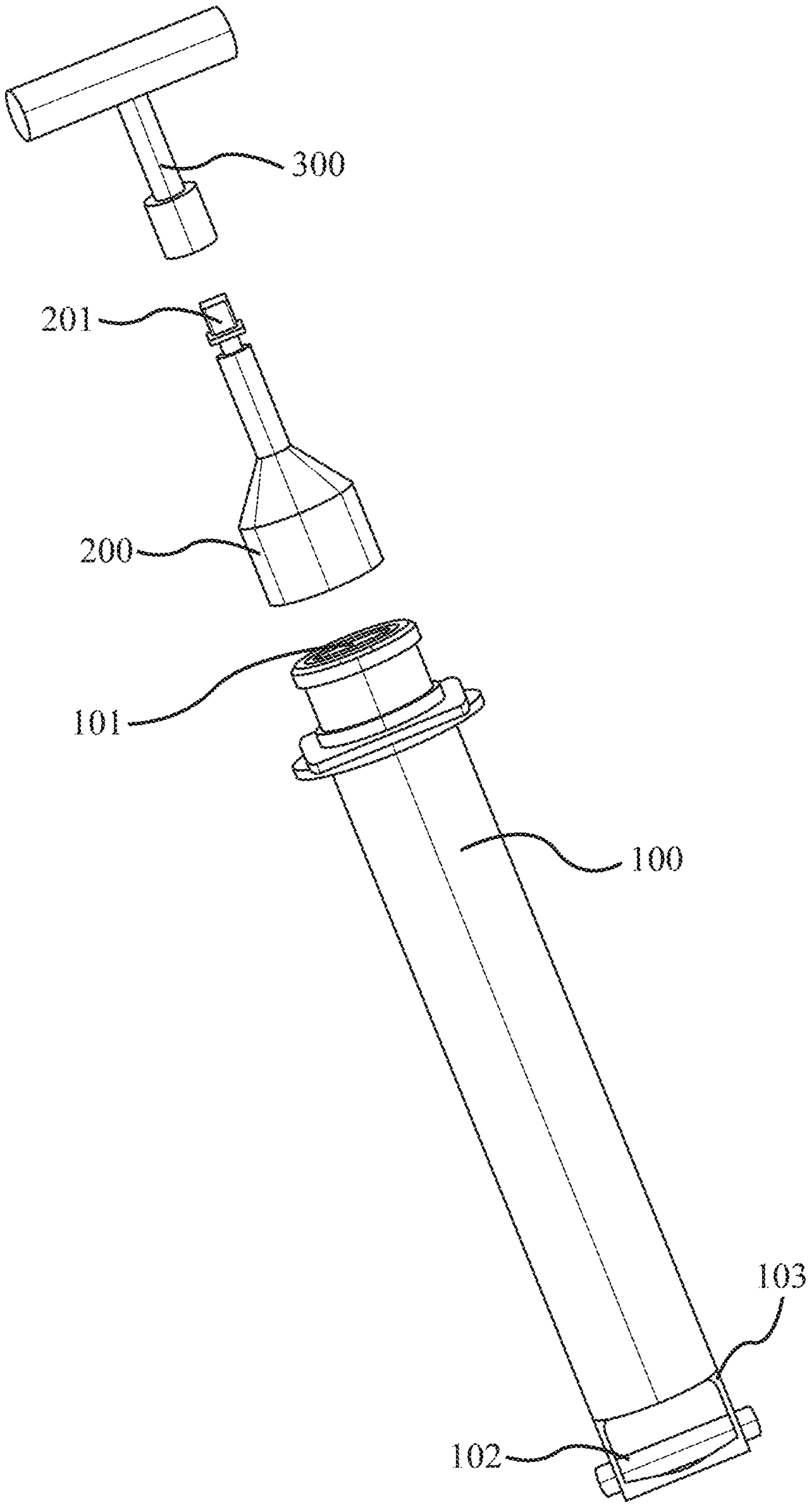
FIG. 1 shows an exploded perspective view of the universal pedicle screw removal system in a preferred embodiment, illustrating the tubular main shaft with its hollow channel, the cross rod at the inferior end, and the tube cap with handle interface at the superior end.

Referring to FIG. 1, an exploded perspective view of the universal pedicle screw removal system in accordance with an exemplary embodiment shows the main body (outside) 100 comprising a tubular main shaft with a hollow channel, the main body (inside) 101, a cross bar 102 connected at the inferior end, a cross bar holding mechanism 103, and a handle 300. The cap 200 includes a connection mechanism 201 with handle interface at the superior aspect.

Figure 2:
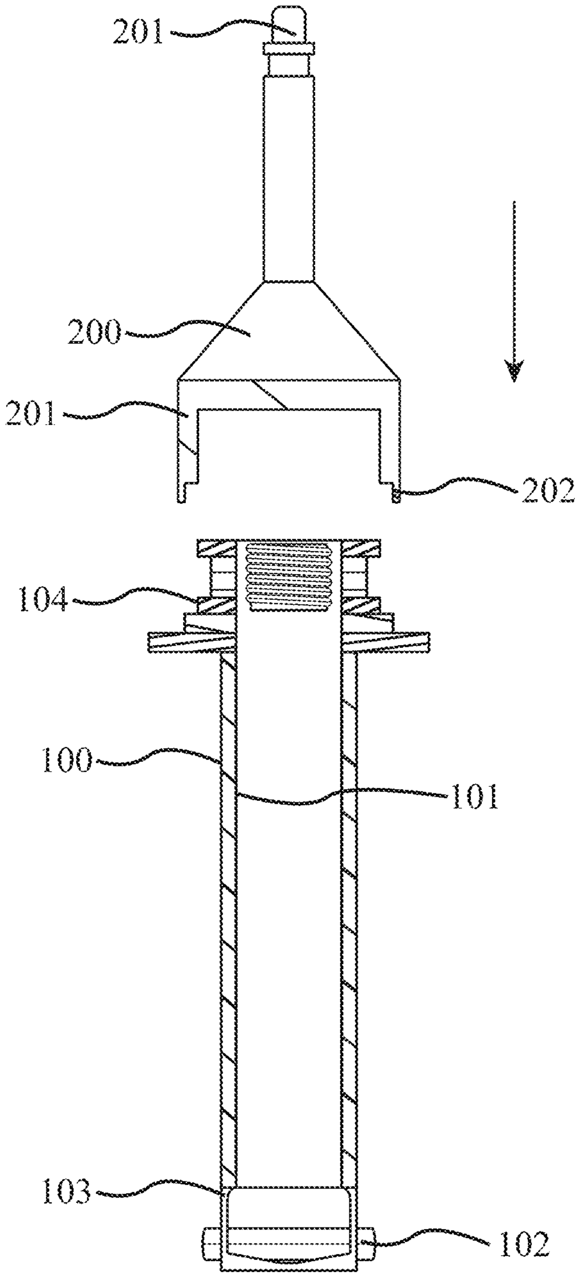
FIG. 2 depicts a cross-sectional view of the assembled device in a preferred embodiment, showing the internal hollow channel of the tubular main shaft and how the geometric configuration of the tube cap interfaces with the superior end of the shaft.

As illustrated in FIG. 2, a cross-sectional view shows the exterior aspect of the main body 100, the interior aspect of the main body 101, cross bar 102, cross bar holding mechanism 103, and a geometric cut out 104. The cap 200 includes a handle interface 201 and an attachment interface 202 configured to interact with the superior end of the shaft in accordance with an exemplary embodiment.

Figure 3:
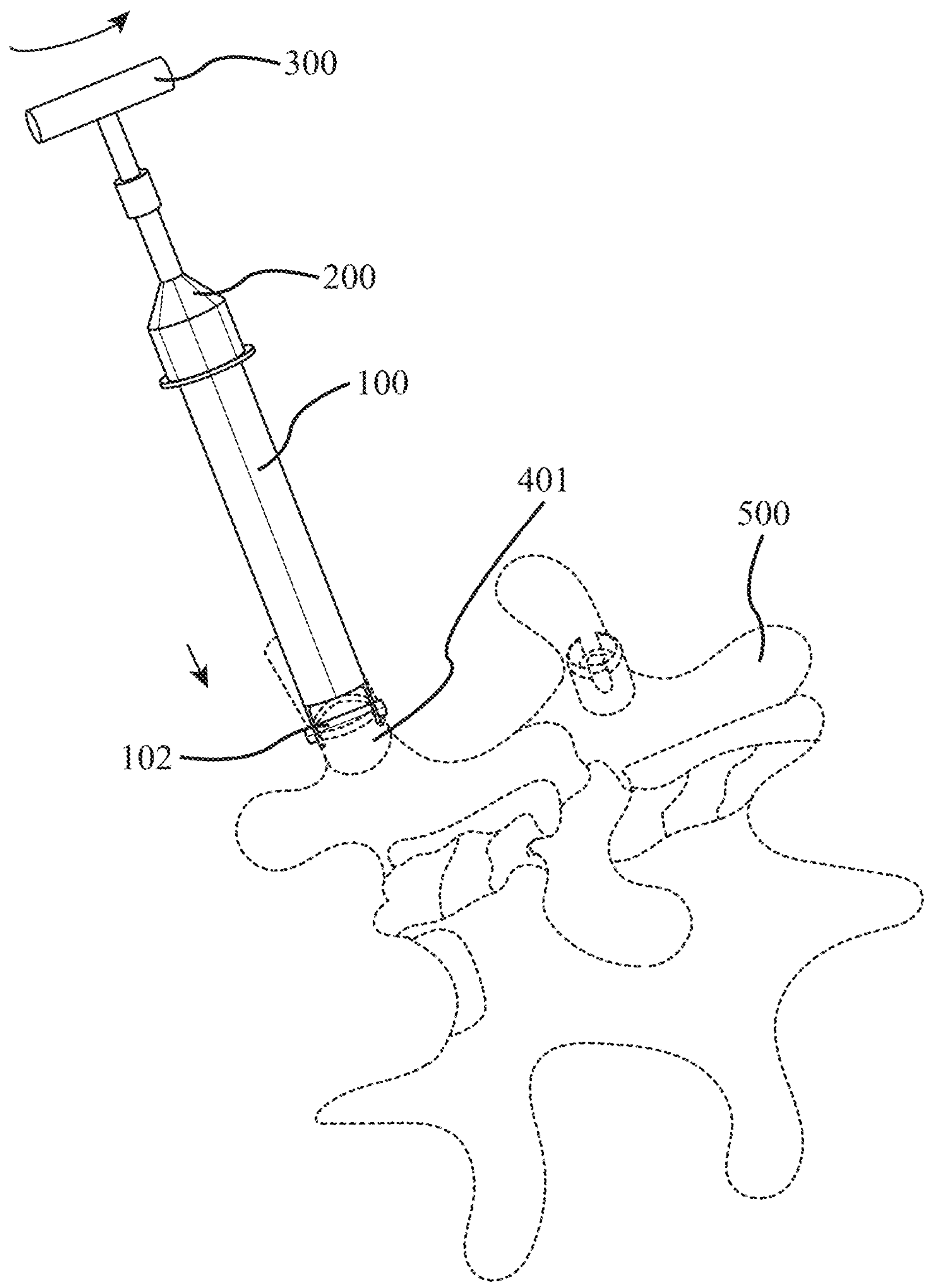
FIG. 3 illustrates the device in use in a preferred embodiment, showing the cross rod positioned within a pedicle screw tulip and secured by the original set screw, with the handle attached to the superior interface for torque application.

FIG. 3 demonstrates the device during use in accordance with an exemplary embodiment, with the main body (outside) 100 positioned with the cross bar 102 within a tulip 401. A handle 300 is shown attached for applying removal torque, with a spinal body 500 visible for context.

Figure 4A:
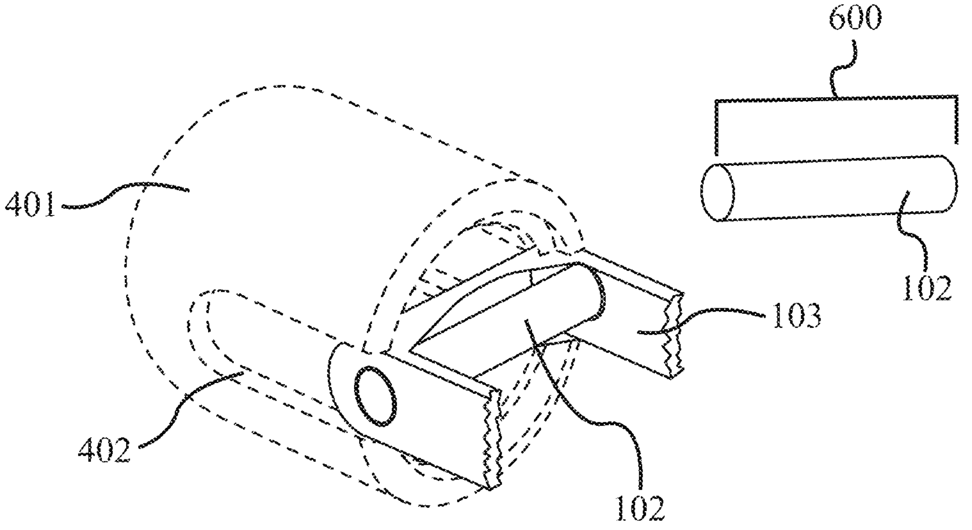
FIG. 4*a* shows a detailed view of a short length cross rod configuration and its engagement with a standard pedicle screw tulip in a preferred embodiment.
Figure 4B:
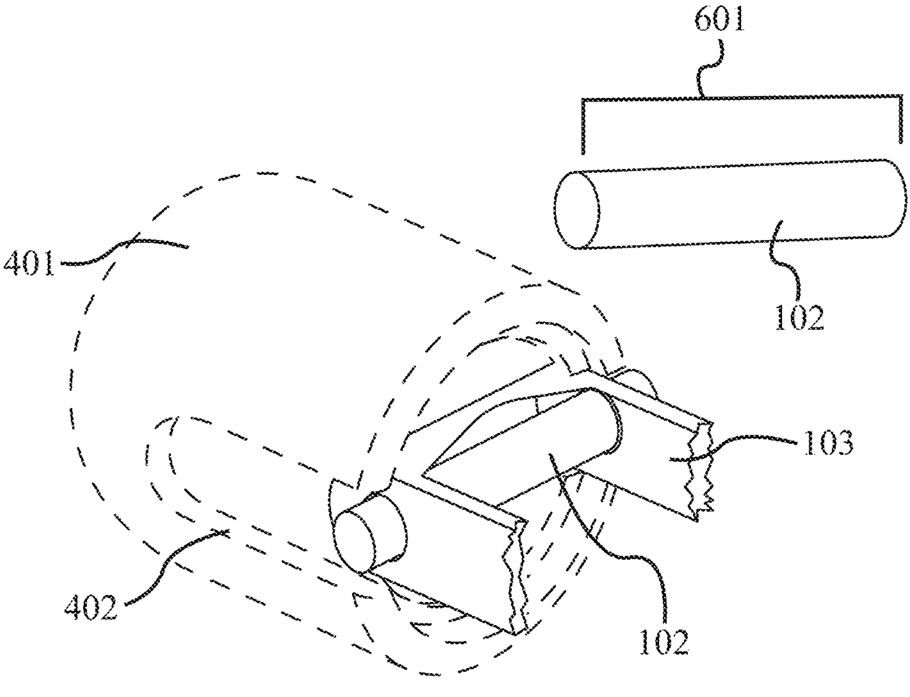
FIG. 4*b* depicts a detailed view of a long length cross rod configuration and its engagement with a standard pedicle screw tulip in a preferred embodiment.
Figure 4C:
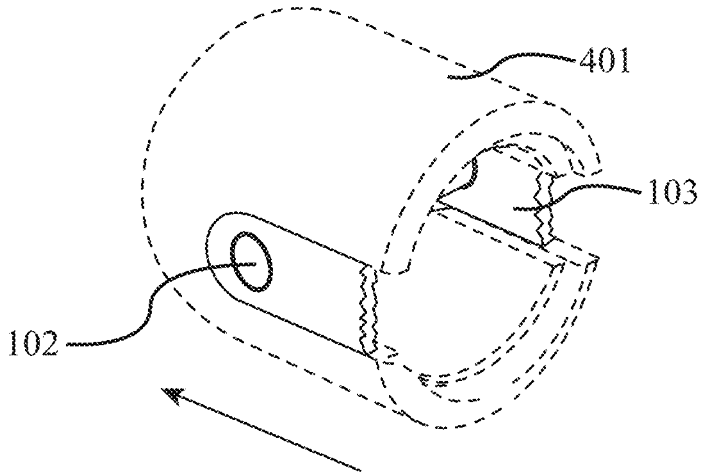
FIG. 4*c* illustrates the placement of the cross rod into the tulip of the pedicle screw prior to placement of the set screw during intended use in accordance with an embodiment.
Figure 4D:
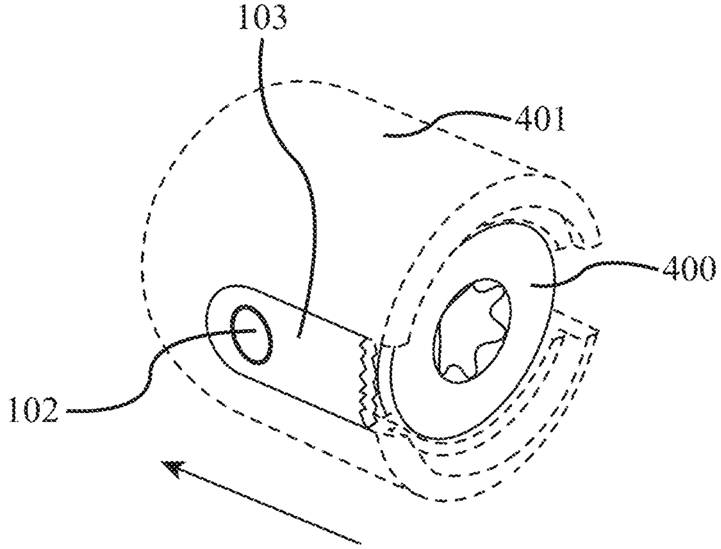
FIG. 4*d* shows the placement of the cross rod into the tulip of the pedicle screw following placement of the set screw during intended use in accordance with an embodiment.
Figure 4E:
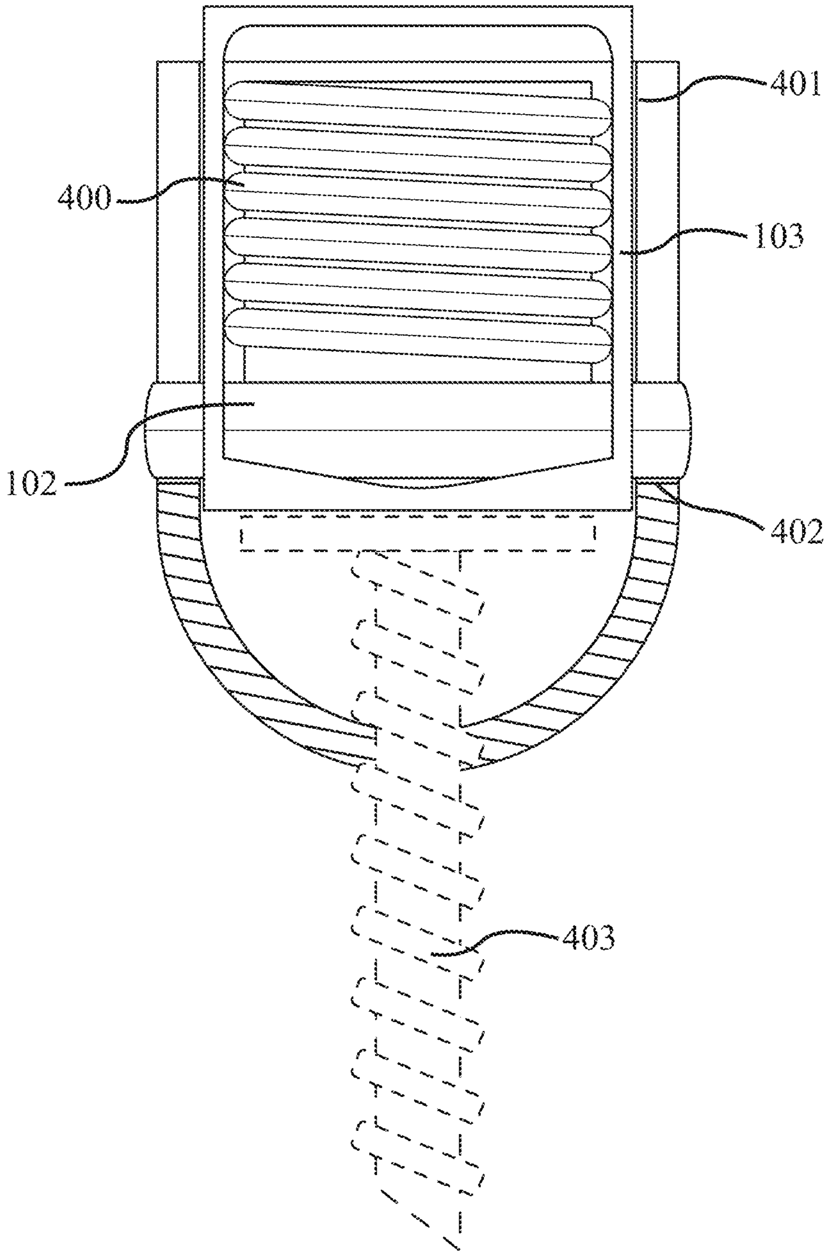
FIG. 4*e* presents a partially cross-sectional view demonstrating placement of the set screw over the cross rod and other aspects of the pedicle screw construction in accordance with an embodiment.

FIGS. 4*a*-4*e* provide views in accordance with an exemplary embodiment of various configurations of the cross bar 102 and its engagement in examples with standard pedicle screw tulips 401, showing compatibility through various configurations including short length bar 600 and long length bar 601 options. FIG. 4*c* shows placement of the cross bar 102 into the tulip of the pedicle screw 401 prior to placement of the set screw during an intended use, while FIG. 4*d* shows placement of the cross bar 102 into the tulip of the pedicle screw 401 following placement of the set screw during an intended use. FIG. 4*e* illustrates a partially cross sectional view of an embodiment of demonstrating placement of the set screw 400 over the cross rod 102, and other aspects of the pedicle screw construction 401-403.

Figure 5A:
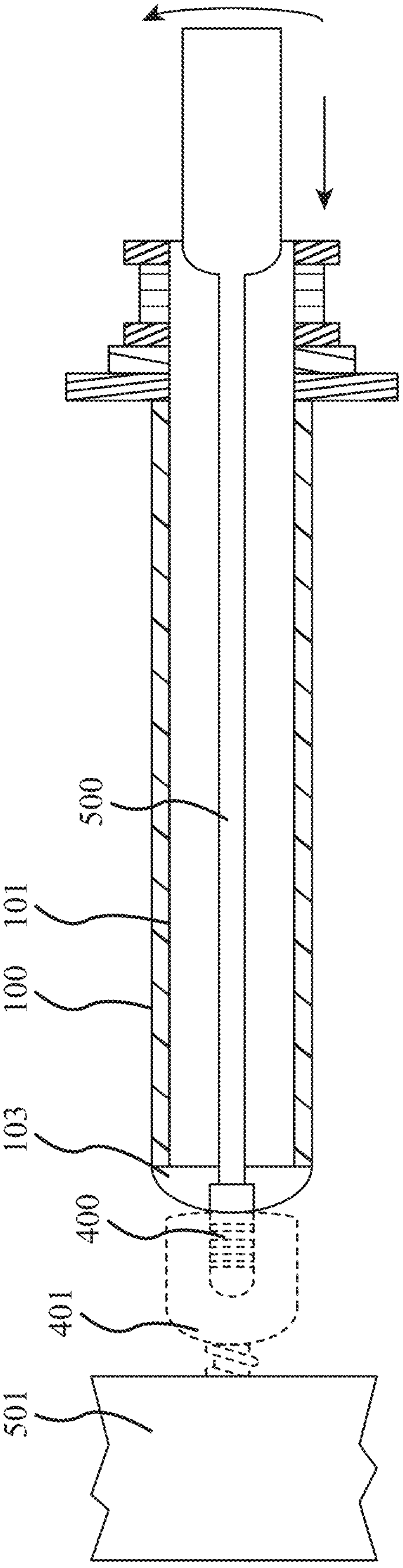
FIG. 5*a* shows connecting to and removing the original set screw through the hollow shaft of the main body, with a bony aspect of a spinal body visible for context in accordance with an embodiment.

FIG. 5 illustrates the sequential steps for using the device in accordance with a preferred embodiment:

FIG. 5*a* shows connecting to and removing the set screw 400 through the main body 100 and main body (inside) 101, with a bony aspect of a spinal body 501 visible for context.

Figure 5B:
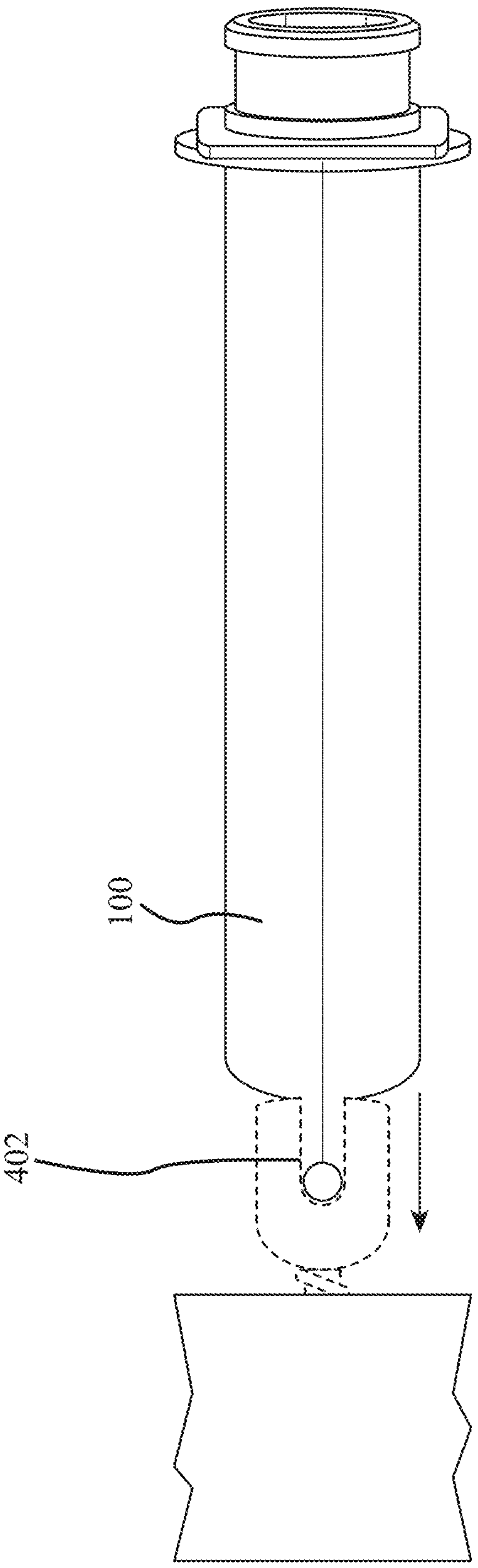
FIG. 5*b* depicts positioning the cross rod within the rod aperture of a pedicle screw tulip in accordance with an embodiment.

FIG. 5*b* depicts positioning within the rod aperture of a pedicle screw tulip 402.

Figure 5C:
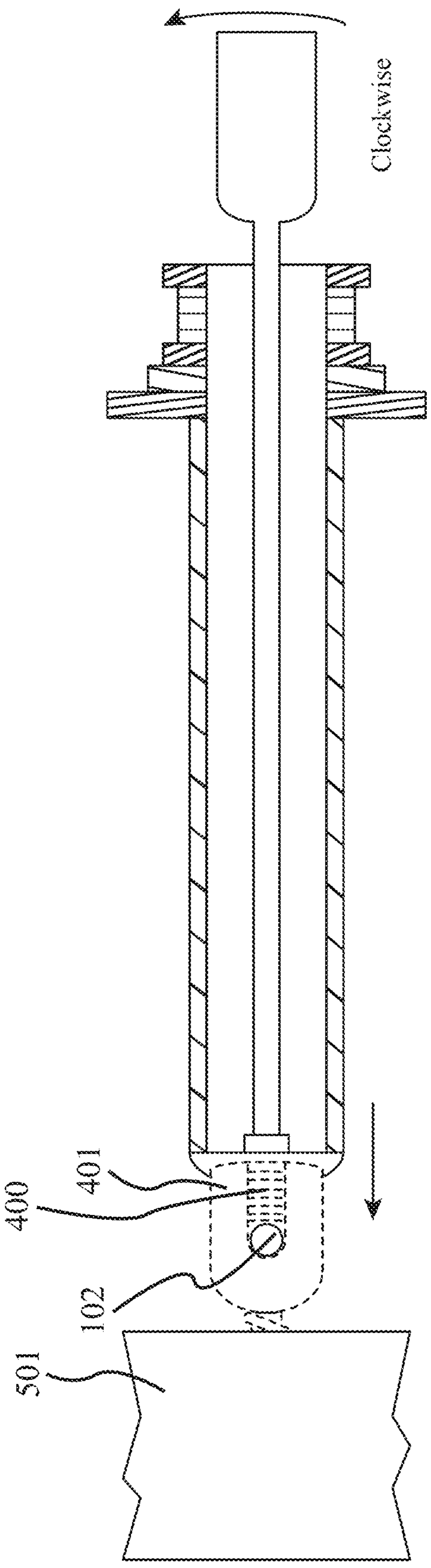
FIG. 5*c* illustrates securing the cross rod by tightening the original set screw over the cross rod in a clockwise direction in accordance with an embodiment.
Figure 5D:
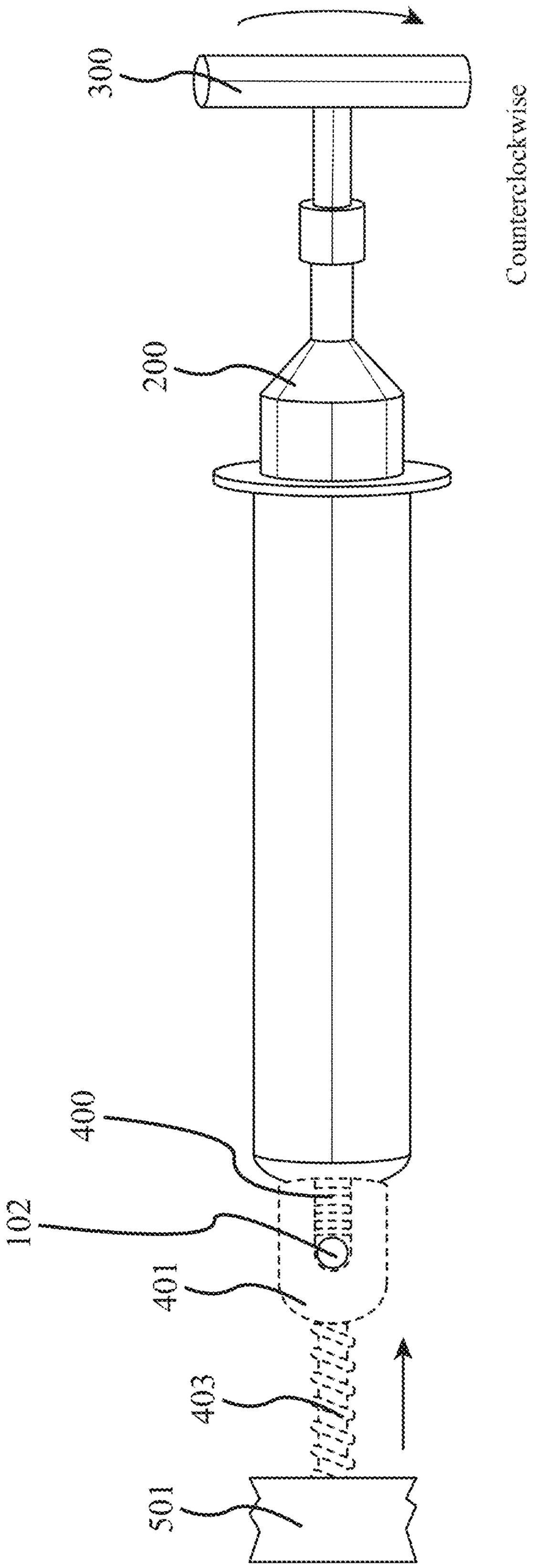
FIG. 5*d* shows applying counterclockwise removal torque via a T-handle through the main body and cross rod, with the screw aspect of the pedicle screw visible for context in accordance with an embodiment.

FIG. 5*c* illustrates securing the cross bar 102 by tightening the set screw 400 over the cross bar in a clockwise direction FIG. 5*d* shows applying counterclockwise removal torque via the handle 300 via the main body 100 through the cross rod 102, with screw aspect of the pedicle screw 403 visible for context.

In one embodiment, the system includes a superior interface configured to accept various handle configurations, including a T-handle, connected to a tubular main shaft having an approximate diameter of 1-2 centimeters. The tubular main shaft is hollow in construction, allowing for the placement and manipulation of set screws through its central channel during the removal procedure. The shaft is specifically designed to accommodate engagement heads of 5.5 millimeters or greater, ensuring broad compatibility across different pedicle screw manufacturers.

At the inferior aspect of the device in a preferred embodiment, a cross rod is connected to the tubular main shaft. This cross rod is engineered to interface with standard pedicle screw tulips and is compatible with common rod sizes, specifically 5.5 and 6.0 millimeter configurations. The cross rod is designed to sit securely in the saddle of the tulip, creating a stable platform for the application of removal torque.

In one embodiment of the invention, the tubular main shaft comprises a hollow cylindrical structure with an approximate diameter of 1-2 centimeters. The hollow design creates a central channel extending longitudinally through the length of the shaft, specifically engineered to allow surgical instruments to pass through for the placement and manipulation of pedicle screw set screws.

The preferred embodiment includes diameter specifications that accommodate engagement heads of 5.5 millimeters or greater, ensuring broad compatibility across different pedicle screw manufacturers and configurations. This dimensional requirement enables the device to interface effectively with standard pedicle screw components while maintaining the structural integrity necessary for torque application during the removal process.

In a preferred embodiment of the invention, the hollow channel serves dual primary functions: facilitating both the initial removal of the original set screw and enabling the subsequent reinstallation and tightening of the same set screw over the cross rod during the removal procedure. This dual-purpose design allows surgeons to complete the entire pedicle screw removal procedure using a single tool system, eliminating the need to change instruments between procedural steps. The hollow channel design enables workflow efficiency by accommodating standard surgical screwdrivers while maintaining compatibility with existing surgical instrument sets, distinguishing it from proprietary systems requiring specialized tools.

The tubular main shaft of one embodiment is designed to work in conjunction with a superior interface that accepts various handle configurations and an inferior cross rod, creating an integrated system for pedicle screw removal. The hollow shaft's specifications allow for compatibility with the vast majority of existing pedicle screw configurations, making it a universal solution for pedicle screw removal procedures.

In one embodiment of the invention, the cross rod is specifically designed for placement into the tulip of a pedicle screw, with features that enable secure positioning and engagement during the removal procedure. The preferred embodiment includes a cross rod configured to be compatible with standard pedicle screw rod sizes, specifically accommodating both 5.5 millimeter and 6.0 millimeter rod dimensions. This standardized sizing ensures broad compatibility since rod sizes are relatively standard across different pedicle screw manufacturers.

The cross rod design of the present invention in accordance with an embodiment comprises a transverse, straight cylindrical member that passes completely through the inferior end of the main shaft as a single, continuous cylindrical element. This straight rod configuration provides significant manufacturing advantages over fork-like designs, including easier fabrication processes and superior structural integrity under high torque applications. The cylindrical cross rod demonstrates enhanced resistance to splaying forces during high-torque removal procedures compared to U-shaped or fork-like engagement members.

The cross rod in accordance with an embodiment maintains precise dimensional specifications with diameters compatible with standard 5.5 mm and 6.0 mm tulip configurations, ensuring consistent engagement across manufacturers while eliminating the potential for component separation or deformation that may occur with multi-piece or bent-rod approaches.

In an example of the invention, the cross rod is engineered to sit securely within the saddle of the pedicle screw tulip. The configuration comprises a cross rod that sits in the saddle of the tulip, with the set screw then positioned into the aperture of the tulip to secure the cross rod in place.

A preferred embodiment features a cross rod design that allows for the reuse of the original set screw that was removed from the pedicle screw, eliminating the need to identify or match specific pedicle screw brands. The cross rod's placement in the tulip saddle, combined with the reinstallation of the original set screw over the cross rod after placement in the tulip saddle, creates a secure connection point that enables controlled application of removal torque through the tubular main shaft.

In one embodiment of the invention, the connection mechanisms include a specialized interface between the cross rod and the tulip aperture, where the cross rod is designed to be secured within the tulip using the original set screw that was removed from the pedicle screw. In an example of the invention, the connection mechanism utilizes the original set screw that was previously removed from the pedicle screw to secure the cross rod within the tulip aperture at the inferior aspect of the system. This innovative approach eliminates the need to identify or match specific pedicle screw brands, as it leverages the existing hardware components. This configuration creates a secure mechanical interface that allows for the effective application of torque through the handle attached at the superior end during the pedicle screw removal process.

In one embodiment of the invention, the superior outer edge of the tubular main shaft comprises a geometric configuration such as a square or hexagonal shape that enables secure attachment of a cap component. The preferred embodiment includes a tube cap for placement over the tubular main shaft, the inferior inner edge of which comprises a compatible geometric configuration corresponding with the geometric configuration of the superior outer edge of the tubular main shaft. The superior aspect of the tube cap in a preferred embodiment further comprises interface that allows for the attachment of various handle configurations, including a T-handle or other handle types. This interface is specifically designed to facilitate the hand-powered application of torque during the pedicle screw removal procedure.

The geometric configuration of the superior interface comprises non-circular cross-sectional shapes including square, hexagonal, or other polygonal configurations with precise manufacturing tolerances that prevent rotational slippage under high removal torques. This mechanical interlock design enables superior torque transfer efficiency compared to simple integrated handle designs, ensuring consistent force transmission from the handle through the main shaft to the cross rod assembly.

The standardized geometric interface provides interchangeability with various handle types while maintaining secure mechanical connection under operational loads. The interface design prevents torque-induced slippage that may occur with less robust connection methods, ensuring reliable performance during high-force screw extraction procedures.

In a preferred embodiment of the invention, the geometric configuration between the tube cap and tubular main shaft creates a mechanically interlocked interface through the mating of corresponding shapes at their connection point. This secure mechanical connection allows torque applied to the handle at the superior aspect to be efficiently transferred through the entire assembly. The standardized interface at the superior aspect of the tube cap enables attachment of various handle types, providing the surgeon with familiar and ergonomic options for applying controlled rotational force necessary for pedicle screw extraction while maintaining the secure connection established by the cross rod and original set screw at the inferior aspect.

In a preferred embodiment of the invention, following the placement and securing of the cross rod within the pedicle screw tulip using the original set screw, the tube cap can be placed over the superior aspect of the tubular main shaft. The geometric configuration of the inferior inner edge of the tube cap is placed upon the superior aspect of the tubular main shaft such that it mates with the corresponding geometric shape of the superior outer edge of the tubular main shaft, creating a secure mechanical connection. Once the tube cap is properly seated on the tubular main shaft, a T-handle or other handle configuration can be attached to the standardized interface at the superior aspect of the tube cap, enabling the surgeon to apply controlled torque for removal of the pedicle screw that has been secured by the cross rod and set screw assembly at the inferior aspect.

In an example of the invention, the tube cap comprises a standardized interface that accommodates common handle configurations, creating an integrated assembly between the superior aspect of the device and the inferior cross rod-set screw mechanism. When assembled, this configuration enables controlled torque application through the handle to the pedicle screw that is secured by the cross rod and original set screw at the inferior aspect of the system.

In one embodiment of the invention, the operational components include mechanisms for both set screw manipulation and handle attachment. The set screw removal and reuse mechanism can be optionally included within the system, though the tubular main shaft is specifically designed to accommodate various existing set screw removal and placement tools that can be passed through its hollow channel. This design flexibility enables surgeons to utilize their preferred instruments for removing the original set screw and subsequently replacing it over the cross rod to secure the pedicle screw.

The preferred embodiment includes a tube cap that comprises a handle placement mechanism engineered to be compatible with common handle configurations utilized in various forms of spine surgery. This standardized interface accommodates T-handles and other handle types, providing flexibility in the choice of torque application tools.

In an example of the invention, the handle attachment system is integrated into the superior aspect of the tube cap, which interfaces with the geometric configuration of the tubular main shaft. While the handle attachment system may be optionally included with the device, the preferred embodiment features a standardized interface that accepts commonly available surgical handles, eliminating the need for specialized proprietary components.

The operational components work in concert to enable a systematic approach to pedicle screw removal: first allowing access for set screw manipulation through the hollow shaft, then providing secure handle attachment for controlled torque application once the cross rod is secured in place.

In one embodiment of the invention, the compatibility features of the system comprise design elements that enable the device to be compatible with the vast majority of existing pedicle screw configurations. This broad compatibility is achieved through careful engineering of key components, including the cross rod dimensions that reflect standard rod sizes of 5.5 or 6.0 millimeters, which are the most commonly used sizes associated with the rods intended to be retained by pedicle screws within the tulip across pedicle screw manufacturers.

The preferred embodiment thus comprises specifications that eliminate the need to identify specific pedicle screw brands or manufacturers. This is accomplished through the innovative use of the original set screw removed from the patient's existing hardware, rather than requiring brand-specific components or specialized removal tools. In an example of the invention, the widespread compatibility is enhanced through the tubular main shaft's diameter specifications, which accommodate engagement heads of 5.5 millimeters or greater. The cross rod is specifically designed to fit any tulip aperture that accepts standard 5.5 or 6.0 millimeter rods, ensuring broad compatibility across different pedicle screw systems. A preferred embodiment comprises a cross rod with dimensions and configurations engineered to be compatible with various pedicle screw brands while maintaining secure engagement when locked in place with the original set screw that a surgeon retrieves from the pedicle screw during the removal process. This compatibility maximizing design approach addresses situations where conventional universal removal sets lack the appropriate bit for the bone screw's proprietary engagement point.

The system in embodiments achieves approximately 98% compatibility with existing pedicle screw configurations through standardized dimensional specifications that align with industry-standard rod sizes of 5.5 mm and 6.0 mm used across multiple manufacturers. This broad compatibility rate eliminates the need for expensive universal removal sets that may cost tens of thousands of dollars while providing incomplete solutions for screw removal challenges.

The cost-effectiveness of the present system compared to comprehensive universal removal sets represents a significant advancement in surgical tool economics. The system's standardized rod size compatibility spans multiple manufacturers without requiring manufacturer identification, addressing the fundamental challenge where conventional universal sets may lack appropriate bits for proprietary engagement points.

In one embodiment of the invention, the usage process begins with accessing the pedicle screw assembly through surgical exposure. In a preferred method of use, the user, typically a surgeon, proceeds by removing the original set screw from the pedicle screw using appropriate instrumentation. Following set screw removal, the surgeon typically removes existing rods that need to be extracted from the pedicle screw assembly, specifically from the tulip of the pedicle screw.

The next phase involves positioning the cross rod, which as described herein is specifically designed to interface with a variety of standard pedicle screw configurations. The surgeon aligns the cross rod with the tulip aperture and carefully inserts it to sit securely in the saddle of the tulip.

After cross rod placement, the previously removed original set screw is reinstalled to the pedicle screw over the cross rod. The set screw is positioned over the cross rod and secured into the pedicle screw, effectively locking the cross rod in place. This innovative approach eliminates the need for additional specialized components by utilizing the patient's existing hardware.

The tubular main shaft features a superior outer edge with a geometric configuration, such as a square or hexagonal shape, designed to accept a tube cap. The tube cap's inferior inner edge comprises a compatible geometric configuration that corresponds with the tubular main shaft's superior outer edge. When placed, this creates a secure mechanical connection that enables efficient transfer of applied torque. The superior aspect of the tube cap incorporates a standardized interface engineered to be compatible with common handle configurations utilized in various forms of spine surgery. This interface accommodates T-handles and other handle types, providing flexibility in the choice of torque application tools while maintaining compatibility with existing surgical equipment.

Once the handle is securely attached to the tube cap's interface, the surgeon can apply controlled torque through the handle. This force is transferred through the mechanically interlocked assembly to the pedicle screw, which is secured by the cross rod and set screw assembly at the inferior aspect. The geometric configuration between the tube cap and tubular main shaft ensures efficient transfer of the applied rotational force necessary for pedicle screw extraction.

The present invention in its preferred embodiment provides a universal pedicle screw removal system designed to address the challenges of extracting previously implanted pedicle screws during spinal surgery. The system comprises a tubular main shaft with a hollow channel that accommodates set screw manipulation, a cross rod for secure engagement with the pedicle screw tulip, and a superior interface that accepts various handle configurations for torque application. This integrated design eliminates the need for extensive universal removal sets by providing compatibility with the vast majority of existing pedicle screw configurations through innovative use of aspects of the original hardware, especially the set screw.

The method of the present invention in an embodiment comprises a specific procedural sequence that differentiates it from ad-hoc removal techniques. The systematic approach includes: (1) accessing the pedicle screw through the hollow shaft for set screw removal, (2) positioning the integrated cross rod within the tulip in a single motion, (3) securing the assembly using the patient's original hardware, and (4) applying controlled torque through the mechanically interlocked handle system. This sequence contrasts with multi-instrument approaches that require assembly of separate components and lack standardized procedural steps.

The method uniquely utilizes the patient's original set screw as a key procedural element, eliminating manufacturer identification requirements and ensuring compatibility with existing hardware. This approach provides controlled torque application through the integrated system design while maintaining procedural consistency across different pedicle screw configurations.

The system's key innovation lies in its compatibility maximizing features to enable removal of a wide variety of pedicle screw configurations, achieved through careful engineering of critical components. The cross rod is designed to interface with standard rod sizes of 5.5 or 6.0 millimeters. The device uniquely enables the reuse of the original set screw removed from the patient's pedicle screw, eliminating the need to identify specific manufacturers or maintain extensive sets of specialized removal bits. The geometric configuration between the tube cap and tubular main shaft creates a mechanically interlocked interface that ensures efficient transfer of applied torque from the handle through the assembly to the secured pedicle screw.

The present invention's pre-fabricated, single-piece integrated design in accordance with an embodiment eliminates the need for intraoperative assembly of multiple components, distinguishing it from ad-hoc surgical techniques that require surgeons to assemble removal apparatus from separate hardware during procedures. Unlike multi-component approaches that may involve rod bending, separate pliers, and various tools assembled during surgery, the present system provides immediate surgical readiness with all components mechanically integrated and optimized for pedicle screw extraction.

This integrated approach provides significant time savings and reduced surgical complexity compared to techniques requiring intraoperative assembly of multiple separate components. The system's reliability advantages stem from eliminating the need for surgeons to manipulate or modify hardware components during critical surgical procedures, thereby reducing procedural variability and potential complications associated with improvised tool configurations.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

I claim:

1. A pedicle screw removal system comprising:

a tubular main shaft having a superior end and an inferior end, the tubular main shaft comprising a hollow channel extending longitudinally therethrough, wherein the hollow channel is configured to allow passage of surgical instruments for manipulation of a set screw;

a cross rod connected to the inferior end of the tubular main shaft, the cross rod configured to be received within a tulip of a pedicle screw; and wherein the superior end of the tubular main shaft comprises a geometric configuration for receiving a handle attachment.

2. The system of claim 1, wherein the tubular main shaft has a diameter between 1-2 centimeters.

3. The system of claim 1, wherein the cross rod is configured to be compatible with pedicle screw rod sizes of 5.5 millimeters and 6.0 millimeters.

4. The system of claim 1, further comprising a tube cap having:

an inferior inner edge comprising a geometric configuration corresponding to the geometric configuration of the superior end of the tubular main shaft; and a superior interface configured to receive a handle.

5. The system of claim 4, wherein the geometric configuration creates a mechanically interlocked interface between the tube cap and the tubular main shaft for transferring torque.

6. The system of claim 1, wherein the cross rod comprises a straight cylindrical member having a diameter selected from the range of 5.5 millimeters to 6.0 millimeters.

7. The system of claim 1, wherein the geometric configuration comprises a non-circular cross-sectional shape selected from the group consisting of square, hexagonal, and polygonal configurations.

8. A method of removing a pedicle screw comprising:

accessing a pedicle screw assembly;

removing an original set screw from the pedicle screw;

removing the original rod;

positioning a cross rod connected to an inferior end of the tubular main shaft within a tulip of the pedicle screw;

securing the cross rod within the tulip using the original set screw;

attaching a handle to a superior end of the tubular main shaft; and applying torque through the handle to remove the pedicle screw.

9. The method of claim 8, further comprising:

placing a tube cap over the superior end of the tubular main shaft, the tube cap having a geometric configuration corresponding to a geometric configuration of the superior end of the tubular main shaft.

10. The method of claim 8, wherein the cross rod is configured to be compatible with pedicle screw rod sizes of 5.5 millimeters and 6.0 millimeters.

11. The method of claim 8, wherein the tubular main shaft has a diameter between 1-2 centimeters.

12. The method of claim 8, further comprising reusing the original set screw removed from the pedicle screw to secure the cross rod, eliminating the need for manufacturer-specific components.

13. The method of claim 8, wherein the method provides compatibility with pedicle screw configurations through standardized dimensional specifications.

14. A pedicle screw removal system comprising:

a tubular main shaft having a superior end and an inferior end, the tubular main shaft comprising a hollow channel extending longitudinally therethrough, wherein the hollow channel is configured to allow passage of surgical instruments for manipulation of a set screw, and wherein the tubular main shaft has a diameter between 1-2 centimeters;

a cross rod connected to the inferior end of the tubular main shaft, the cross rod configured to be received within a tulip of a pedicle screw; and wherein the superior end of the tubular main shaft comprises a geometric configuration for receiving a handle attachment.

15. The system of claim 14, wherein the cross rod is configured to be compatible with pedicle screw rod sizes of 5.5 millimeters and 6.0 millimeters.

16. The system of claim 14, further comprising a tube cap having:

an inferior inner edge comprising a geometric configuration corresponding to the geometric configuration of the superior end of the tubular main shaft; and a superior interface configured to receive a handle.

17. The system of claim 16, wherein the geometric configuration creates a mechanically interlocked interface between the tube cap and the tubular main shaft for transferring torque.

18. The system of claim 14, wherein the cross rod comprises a straight cylindrical member having a diameter selected from the range of 5.5 millimeters to 6.0 millimeters.

19. The system of claim 14, wherein the geometric configuration comprises a non-circular cross-sectional shape selected from the group consisting of square, hexagonal, and polygonal configurations.

* * * * *